United States Patent
Paul et al.

(10) Patent No.: US 11,285,177 B2
(45) Date of Patent: Mar. 29, 2022

(54) ALLOGRAFTS CONTAINING VIABLE CELLS AND METHODS THEREOF

(71) Applicant: GLOBUS MEDICAL, INC., Audubon, PA (US)

(72) Inventors: David C. Paul, Phoenixville, PA (US); Archana Bhat, Phoenixville, PA (US); Breanna Seiber, Philadelphia, PA (US)

(73) Assignee: Globus Medical, Inc., Audubon, PA (US)

( * ) Notice: Subject to any disclaimer, the term of this patent is extended or adjusted under 35 U.S.C. 154(b) by 0 days.

(21) Appl. No.: 16/210,464

(22) Filed: Dec. 5, 2018

(65) Prior Publication Data

US 2019/0201451 A1     Jul. 4, 2019

Related U.S. Application Data

(60) Provisional application No. 62/613,107, filed on Jan. 3, 2018.

(51) Int. Cl.
    *A61K 35/32*     (2015.01)
    *A61K 38/39*     (2006.01)
    (Continued)

(52) U.S. Cl.
    CPC ............ *A61K 35/32* (2013.01); *A01N 1/0221* (2013.01); *A61K 31/728* (2013.01); *A61K 35/33* (2013.01); *A61K 38/39* (2013.01); *A61L 27/3821* (2013.01); *A61L 2300/412* (2013.01); *A61L 2400/18* (2013.01); *A61L 2430/02* (2013.01)

(58) Field of Classification Search
    CPC .. A61K 2300/00; A61K 31/728; A61K 35/32; A61K 35/33; A61K 38/39; A61K 35/51; A61K 9/0024; A01N 1/0221; A61L 2300/412; A61L 2400/06; A61L 2400/18; A61L 2430/02; A61L 2430/38; A61L 27/3604; A61L 27/3612; A61L 27/3658; A61L 27/3687; A61L 27/3821
See application file for complete search history.

(56) References Cited

U.S. PATENT DOCUMENTS 5,155,034 A     10/1992    Wolf et al.
5,256,418 A     10/1993    Kemp et al.
(Continued)

FOREIGN PATENT DOCUMENTS

RU     2071737 C1    1/1997
RU     2455353 C1    7/2012
(Continued)

OTHER PUBLICATIONS

Tan et al. (Materials 2010;3:1746-1767). (Year: 2010).*
(Continued)

*Primary Examiner* — Ernst V Arnold

(57) ABSTRACT

Allograft biomaterials, implants made therefrom, methods of making the biomaterial and implants, methods of promoting cartilage, tissue, bone or wound healing in a mammal by administering the biomaterial or implant to the mammal, and kits that include such biomaterials, implants, or components thereof. For example, the allograft may include viable cells, for example, which were native to intervertebral discs and/or umbilical cords that the allograft was derived from.

12 Claims, 2 Drawing Sheets

(51) Int. Cl.
  *A61K 35/51* (2015.01)
  *A61L 27/36* (2006.01)
  *A61K 35/33* (2015.01)
  *A01N 1/02* (2006.01)
  *A61L 27/38* (2006.01)
  *A61K 31/728* (2006.01)

(56) References Cited

U.S. PATENT DOCUMENTS

| | | | |
|---|---|---|---|
| 5,496,722 A | 3/1996 | Goodwin et al. | |
| 5,585,116 A | 12/1996 | Boniface et al. | |
| 5,964,807 A | 10/1999 | Gan et al. | |
| 6,080,579 A | 6/2000 | Hanley, Jr. et al. | |
| 6,152,142 A | 11/2000 | Tseng | |
| 6,326,019 B1 | 12/2001 | Tseng | |
| 6,340,369 B1 | 1/2002 | Ferree | |
| 6,344,058 B1 | 2/2002 | Ferree | |
| 6,696,073 B2 | 2/2004 | Boyce et al. | |
| 6,730,124 B2 | 5/2004 | Steiner | |
| 6,752,831 B2 | 6/2004 | Sybert et al. | |
| 6,890,354 B2 | 5/2005 | Steiner et al. | |
| 6,916,655 B2 | 7/2005 | Yasumoto et al. | |
| 7,101,545 B1 | 9/2006 | Hanley, Jr. et al. | |
| 7,137,996 B2 | 11/2006 | Steiner et al. | |
| 7,141,066 B2 | 11/2006 | Steiner et al. | |
| 7,156,877 B2 | 1/2007 | Lotz et al. | |
| 7,201,773 B2 | 4/2007 | Steiner et al. | |
| 7,294,144 B1 | 11/2007 | Schneider | |
| 7,309,356 B2 | 12/2007 | Steiner | |
| 7,445,776 B2 | 11/2008 | Hanley, Jr. et al. | |
| 7,510,873 B2 | 3/2009 | Mistry et al. | |
| 7,547,546 B2 | 6/2009 | Davies et al. | |
| 7,556,649 B2 | 7/2009 | Moehlenbruck et al. | |
| 7,909,886 B2 | 3/2011 | Carr, Jr. et al. | |
| 7,931,687 B2 | 4/2011 | Masuda et al. | |
| 8,067,397 B2 | 11/2011 | Attawia et al. | |
| 8,153,162 B2 | 4/2012 | Tseng et al. | |
| 8,163,554 B2 | 4/2012 | Kandel | |
| 8,187,639 B2 | 5/2012 | Tseng et al. | |
| 8,227,246 B2 | 7/2012 | Kukekov et al. | |
| 8,273,347 B2 | 9/2012 | Attawia et al. | |
| 8,277,794 B2 | 10/2012 | Davies et al. | |
| 8,278,101 B2 | 10/2012 | Navran, Jr. | |
| 8,278,102 B2 | 10/2012 | Ennis et al. | |
| 8,287,854 B2 | 10/2012 | Phan | |
| 8,318,483 B2 | 11/2012 | Mistry et al. | |
| 8,333,960 B2 | 12/2012 | Attawia et al. | |
| 8,367,409 B2 | 2/2013 | Abbot et al. | |
| 8,383,095 B2 | 2/2013 | Christensen et al. | |
| 8,455,009 B2 | 6/2013 | Tseng et al. | |
| 8,460,714 B2 | 6/2013 | Tseng et al. | |
| 8,481,311 B2 | 7/2013 | Davies et al. | |
| 8,652,503 B2 * | 2/2014 | Wironen | A61L 27/227 424/423 |
| 8,734,827 B2 | 5/2014 | Chan et al. | |
| 8,790,923 B2 | 7/2014 | Ennis et al. | |
| 8,815,587 B2 | 8/2014 | Harris et al. | |
| 8,834,928 B1 | 9/2014 | Truncale et al. | |
| 8,900,573 B2 | 12/2014 | Davies et al. | |
| 9,018,005 B2 | 4/2015 | Lim et al. | |
| 9,029,146 B2 | 5/2015 | Lim et al. | |
| 9,040,299 B2 | 5/2015 | Phan | |
| 9,044,335 B2 | 6/2015 | Bonassar et al. | |
| 9,085,755 B2 | 7/2015 | Phan et al. | |
| 9,114,190 B2 | 8/2015 | Flood | |
| 9,161,954 B2 | 10/2015 | Tseng et al. | |
| 9,161,955 B2 | 10/2015 | Tseng et al. | |
| 9,161,956 B2 | 10/2015 | Tseng et al. | |
| 9,198,939 B2 | 12/2015 | Tseng et al. | |
| 9,283,013 B2 | 3/2016 | Shimko et al. | |
| 9,315,776 B2 | 4/2016 | Fong et al. | |
| 9,387,094 B2 | 7/2016 | Manrique et al. | |
| 9,452,185 B2 | 9/2016 | Gregory et al. | |
| 9,487,753 B2 | 11/2016 | Kukekoev et al. | |
| 9,498,501 B2 | 11/2016 | Mistry et al. | |
| 9,517,128 B2 | 12/2016 | McAlpine et al. | |
| 9,526,770 B2 | 12/2016 | Tseng et al. | |
| 9,567,564 B2 | 2/2017 | Davies et al. | |
| 9,603,710 B2 | 3/2017 | Shi et al. | |
| 9,611,456 B2 | 4/2017 | Davies et al. | |
| 9,649,342 B2 | 5/2017 | Flood | |
| 9,655,928 B2 | 5/2017 | Temple | |
| 9,655,929 B2 | 5/2017 | Temple | |
| 9,655,994 B2 | 5/2017 | McKay | |
| 9,657,270 B2 | 5/2017 | Kukekov et al. | |
| 9,662,420 B2 | 5/2017 | Bonassar et al. | |
| 9,675,733 B2 | 6/2017 | Tseng et al. | |
| 9,682,044 B2 | 6/2017 | Tseng et al. | |
| 9,682,160 B2 | 6/2017 | Tseng et al. | |
| 9,717,763 B2 | 8/2017 | Mistry et al. | |
| 9,737,568 B2 | 8/2017 | Phan et al. | |
| 9,750,772 B2 | 9/2017 | Tseng et al. | |
| 9,803,176 B2 | 10/2017 | Patel | |
| 9,844,571 B2 | 12/2017 | Phan et al. | |
| 2003/0211602 A1 | 11/2003 | Atala | |
| 2004/0067480 A1 * | 4/2004 | Brockbank | A01N 1/0221 435/1.1 |
| 2004/0197367 A1 | 10/2004 | Rezania et al. | |
| 2004/0197375 A1 | 10/2004 | Rezania et al. | |
| 2005/0118147 A1 | 6/2005 | Oh | |
| 2005/0118714 A1 | 6/2005 | Ha et al. | |
| 2005/0158397 A1 | 7/2005 | Chopp et al. | |
| 2005/0244963 A1 | 11/2005 | Teplyashin | |
| 2006/0057720 A1 | 3/2006 | Xu et al. | |
| 2006/0147424 A1 | 7/2006 | Sakuragawa et al. | |
| 2006/0182724 A1 | 8/2006 | Riordan | |
| 2007/0128722 A1 | 6/2007 | Lin et al. | |
| 2008/0014179 A1 * | 1/2008 | Ferree | C12N 5/0655 424/93.7 |
| 2008/0085292 A1 | 4/2008 | Rezania et al. | |
| 2008/0102506 A1 | 5/2008 | Teplyashin | |
| 2008/0118477 A1 | 5/2008 | Christopherson | |
| 2008/0152630 A1 | 6/2008 | Ginis et al. | |
| 2009/0068153 A1 | 3/2009 | Vitelli et al. | |
| 2009/0170059 A1 | 7/2009 | Klingemann | |
| 2009/0232781 A1 | 9/2009 | Fu | |
| 2009/0232782 A1 | 9/2009 | Fu | |
| 2009/0280093 A1 | 11/2009 | Friedlander | |
| 2010/0119492 A1 | 5/2010 | Hans et al. | |
| 2010/0260721 A1 | 10/2010 | McGonagie et al. | |
| 2010/0274355 A1 | 10/2010 | McGuire et al. | |
| 2010/0331197 A1 | 12/2010 | Fortunel | |
| 2011/0008298 A1 | 1/2011 | Lim et al. | |
| 2011/0117171 A1 | 5/2011 | Melican et al. | |
| 2011/0143433 A1 | 6/2011 | Oh et al. | |
| 2011/0151555 A1 | 6/2011 | Shamblott et al. | |
| 2011/0262486 A1 | 10/2011 | Tsai et al. | |
| 2011/0263001 A1 | 10/2011 | Shamblott et al. | |
| 2011/0293667 A1 | 12/2011 | Baksh et al. | |
| 2012/0100607 A1 | 4/2012 | Duntsch et al. | |
| 2012/0141595 A1 | 6/2012 | Tseng et al. | |
| 2012/0219531 A1 | 8/2012 | Oh et al. | |
| 2012/0264623 A2 | 10/2012 | Fortunel et al. | |
| 2013/0216505 A1 | 8/2013 | Patel | |
| 2013/0302887 A1 | 11/2013 | Shamblott et al. | |
| 2013/0344163 A1 | 12/2013 | Tseng et al. | |
| 2014/0271779 A1 * | 9/2014 | Bagga | A61L 27/46 424/426 |
| 2014/0335062 A1 | 11/2014 | Hare | |
| 2014/0342014 A1 | 11/2014 | Tseng et al. | |
| 2014/0343688 A1 | 11/2014 | Morse et al. | |
| 2015/0010506 A1 | 1/2015 | Jansen et al. | |
| 2015/0151858 A1 | 6/2015 | Turzi | |
| 2015/0164952 A1 | 6/2015 | Mahmud | |
| 2015/0197725 A1 | 7/2015 | Lim et al. | |
| 2015/0203814 A1 | 7/2015 | Tseng et al. | |
| 2015/0246079 A1 | 9/2015 | Davies et al. | |
| 2015/0327891 A1 | 11/2015 | Brahm | |
| 2016/0102292 A1 | 4/2016 | Phan | |
| 2016/0106785 A1 | 4/2016 | Tseng et al. | |
| 2016/0129051 A1 | 5/2016 | Tseng et al. | |
| 2016/0158292 A1 | 6/2016 | Alt et al. | |
| 2016/0184368 A1 | 6/2016 | Tseng et al. | |
| 2016/0192973 A1 | 7/2016 | Shimko et al. | |

(56) References Cited

U.S. PATENT DOCUMENTS

| | | |
|---|---|---|
| 2016/0199537 A1 | 7/2016 | Koob |
| 2016/0235790 A1 | 8/2016 | Gurney et al. |
| 2016/0303171 A1 | 10/2016 | Tseng et al. |
| 2016/0324902 A1 | 11/2016 | Tseng et al. |
| 2016/0339061 A1 | 11/2016 | Tseng et al. |
| 2016/0354518 A1 | 12/2016 | Xu |
| 2016/0361171 A1 | 12/2016 | Wang et al. |
| 2016/0376305 A1 | 12/2016 | Tseng et al. |
| 2017/0029770 A1 | 2/2017 | Bopardikar et al. |
| 2017/0049820 A1 | 2/2017 | Shoemaker et al. |
| 2017/0072102 A1 | 3/2017 | Tseng et al. |
| 2017/0073640 A1 | 3/2017 | Kukekov et al. |
| 2017/0119824 A1 | 5/2017 | Venkataramanaa |
| 2017/0157180 A1 | 6/2017 | Davies et al. |
| 2017/0224736 A1 | 8/2017 | Alt et al. |
| 2017/0224874 A1 | 8/2017 | Maki et al. |
| 2017/0226482 A1 | 8/2017 | Lee et al. |
| 2017/0239050 A1 | 8/2017 | Vickers |
| 2017/0239389 A1 | 8/2017 | Tseng et al. |
| 2017/0252483 A1 | 9/2017 | McKay |
| 2017/0258727 A1 | 9/2017 | Tseng et al. |
| 2017/0296588 A1 | 10/2017 | Ichim et al. |
| 2017/0326183 A1 | 11/2017 | Mistry et al. |
| 2017/0335283 A1 | 11/2017 | Wang et al. |
| 2017/0335286 A1 | 11/2017 | Zamilpa et al. |
| 2018/0000866 A1 | 1/2018 | Phan et al. |

FOREIGN PATENT DOCUMENTS

| | | |
|---|---|---|
| RU | 2455357 C1 | 7/2012 |
| WO | 2007071048 A1 | 6/2007 |

OTHER PUBLICATIONS

Galbusera and Hans-Joachim Wilke (Biomechanics of the Spine: Basic Concepts, Spinal Disorders and Treatments; Academic Press, Apr. 23, 2018—Technology & Engineering; p. 54). 1 page (Year: 2018).*

Capossela et al. (European Cells and Materials 2014;27:251-263). (Year: 2014).*

Cold Spring Harbor Protocols ([online] retrieved from: http://cshprotocols.cshlp.org/content/2017/11/pdb.rec095331.full?text_only=true; 2017; 1 page). (Year: 2017).*

Chou et al. (Stem Cell Research & Therapy (2016) 7:89; 10 pages). (Year: 2016).*

Valeri et al. (Transfusion 1996;36:303-308) (Year: 1996).*

* cited by examiner

ALLOGRAFTS CONTAINING VIABLE CELLS AND METHODS THEREOF

CROSS-REFERENCE TO RELATED APPLICATION

This application claims priority to U.S. Provisional Application No. 62/613,107, filed Jan. 3, 2018, which incorporated by reference herein in its entirety for all purposes.

TECHNICAL FIELD

The present invention relates generally to bone, cartilage, and tissue healing biomaterials, and in particular, allogenic biomaterials containing viable cells. The invention also relates to methods of making the materials and implants, for example, derived from intervertebral discs and/or umbilical cords, and methods of promoting bone, cartilage, or wound healing in a mammal by administering the biomaterial or implant to the mammal. The invention further relates to kits that include one or more of the biomaterials, implants, or components thereof.

BACKGROUND

Bone, cartilage, or tissue grafting is a surgical procedure that replaces missing bone, cartilage, or tissue and/or repairs bone, cartilage, or tissue. Bone, cartilage, and tissue generally have the ability to regenerate well but may require a scaffold or other growth enhancers to do so effectively. Grafts may be allograft (e.g., cadaveric origin or live donors), autologous (e.g., bone or tissue harvested from the patient's own body), or synthetic. Bone, cartilage, and/or tissue grafts may be resorbed and replaced as the natural bone, cartilage, or tissue heals over time.

For cartilage, successful biomaterials may promote chondrogenesis, the process by which cartilage is developed. For bone, successful biomaterials may include osteoconduction (guiding the reparative growth of the natural bone or tissue), osteoinduction (encouraging undifferentiated cells to become active osteoblasts), and/or osteogenesis (living bone cells in the graft material contributing to bone or tissue remodeling). For other tissues, successful biomaterials may include other suitable pathways or properties to enhance tissue formation and development. Although traditional grafts may exhibit certain advantages, traditional allograft may not exhibit the properties desired, may be difficult to obtain, or may not be in a shape or form suitable for implantation.

SUMMARY

To meet this and other needs, allograft biomaterials described herein may be configured to promote tissue, bone, and/or cartilage healing and repair. The allograft compositions or implants prepared therefrom may be derived, for example, from intervertebral discs and/or umbilical cords. In an exemplary embodiment, the allograft includes viable cells, for example, which were native to the intervertebral discs and/or umbilical cords that the allograft was derived from. The allografts may be particularly suitable for use in cartilage, bone, or other tissue healing or when living cells are needing during a surgical procedure.

According to one embodiment, a composition for aiding tissue regeneration includes allograft particles derived from human intervertebral disc comprising native collagen, native proteoglycan, and native viable cells. The native viable cells may include one or more of chondrocytic cells, notochordal cells, nucleus pulposus stem/progenitor cells, fibrocytic cells, and combinations thereof. The native collagen may include collagen I, collagen II, or both. The allograft may be derived from the nucleus pulposus, the annulus fibrosus, or both of the components of the intervertebral disc. The particles may have a particle size, for example, ranging from about 250 microns to about 3 mm. The composition may further include a cryoprotectant, which may be decanted prior to use, a carrier solution, or other component. If present, the carrier solution may include one or more of hyaluronic acid (HA), collagen, aggrecan, chondroitin sulfate, and polyethylene glycol (PEG).

According to another embodiment, a method of preparing an implantable composition for aiding tissue regeneration may include obtaining intervertebral disc from a human subject; washing the intervertebral disc with a phosphate buffered saline solution containing antibiotics; and milling the intervertebral disc into particles to form the implantable composition. The method may further include one or more of the following steps: rinsing the particles, for example, with saline; combining the particles with a cryoprotectant to form a mixture, and freezing the mixture, for example, at a temperature of from −80° C. to −180° C.; thawing the mixture and decanting the cryoprotectant before use; combining the particles with a carrier solution containing one or more of hyaluronic acid (HA), collagen, aggrecan, chondroitin sulfate, and polyethylene glycol (PEG); culturing the particles in a medium to obtain particles with proliferated cells; and/or treating the particles with an enzyme.

According to another embodiment, a composition for aiding tissue regeneration may include a patch derived from umbilical cord comprising native viable cells including native epithelial stem cells and native mesenchymal stem cells. The patch may include an upper layer of native Wharton's jelly and a lower layer of native epithelium.

According to another embodiment, a method of preparing an implantable composition for aiding tissue regeneration may include obtaining umbilical cord from a human subject; separating and removing the veins and arteries from the umbilical cord; processing the umbilical cord into a patch to form the implantable composition. The method may further include one or more of the following steps: rinsing the umbilical cord, for example, with saline; milling the umbilical cord into particles; combining the particles with a cryoprotectant to form a mixture, and freezing the mixture, for example, at a temperature of from −80° C. to −180° C.; thawing the mixture and decanting the cryoprotectant before use; treating the umbilical cord with an enzyme to decellularize part or all of the patch; and/or seeding the umbilical cord, for example, with exogenous mesenchymal stem cells isolated from bone or bone marrow aspirate.

According to yet another embodiment, a method of promoting bone, disc, tissue, or wound healing in a mammal may include providing an allograft composition, for example, including allograft derived from intervertebral disc and/or umbilical cord; and administering the composition into a target repair site to facilitate repair or regeneration of tissue at the target repair site. The target repair site may be an injury or defect in the spine and the tissue being regenerated is bone or intervertebral disc.

According to yet another embodiment, a kit includes one or more of the components, compositions, or implants described herein, retrieval kits, trays, syringes, or other components for combining and administering the biomaterial components. For example, the kit may contain powder, putty, gel, strip, and/or extrudable versions of the compositions. The kit may contain compositions of the same or different types. In addition, the kit may include other components known in the art, including, but not limited to, carriers or scaffolds, cages (e.g., titanium and/or polyether ether ketone (PEEK) spacers), allograft spacers, cell culture media, phosphate buffered saline (PBS), a tissue culture substrate, retrieval tools, harvesting tools, implantation tools, or the like.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

Figure 1:
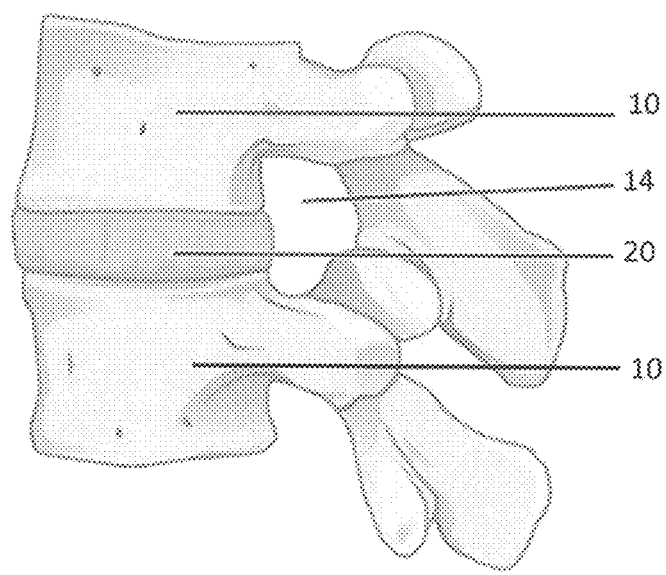
FIG. 1 depicts a lateral view of an intervertebral disc between two adjacent vertebrae.

The present invention relates generally to allograft biomaterial compositions and implants made therefrom that may be used in a variety of surgical procedures. The invention also relates to methods of making the compositions and implants, and methods of promoting bone, cartilage, tissue, or wound healing in a mammal by administering the biomaterial or implant to the mammal. The invention further relates to kits that include one or more of the biomaterials, implants, retrieval kits, tools and trays for mixing and combining ingredients, and other components thereof.

Additional aspects, advantages and/or other features of example embodiments of the invention will become apparent in view of the following detailed description. It should be apparent to those skilled in the art that the described embodiments provided herein are merely exemplary and illustrative and not limiting. Numerous embodiments of modifications thereof are contemplated as falling within the scope of this disclosure and equivalents thereto.

In describing example embodiments, specific terminology is employed for the sake of clarity. However, the embodiments are not intended to be limited to this specific terminology. Unless otherwise noted, technical terms are used according to conventional usage.

As used herein, "a" or "an" may mean one or more. As used herein "another" may mean at least a second or more. As used herein, unless otherwise required by context, singular terms include pluralities and plural terms include the singular.

As used herein and in the claims, the terms "comprising" and "including" are inclusive or open-ended and do not exclude additional unrecited elements, compositional components, or method steps. Accordingly, the terms "comprising" and "including" encompass the more restrictive terms "consisting essentially of" and "consisting of."

Unless specified otherwise, all values provided herein include up to and including the endpoints given, and the values of the constituents or components of the compositions are expressed in weight percent or % by weight of each ingredient in the composition.

Each compound or name used herein may be discussed interchangeably with respect to its chemical formula, chemical name, abbreviation, acronym, etc. For example, BMP may be used interchangeably with bone morphogenic protein.

Embodiments described herein may be generally directed to allograft biomaterial compositions, implants made therefrom, methods of making the same, and methods of using the same to promote healing of tissue, cartilage repair, and/or fusion of bone. Although compositions, biomaterials or implants may be discussed separately, it will be appreciated by one of ordinary skill in the art that the compositions or biomaterials described may be used in and of itself or may be used to create implants of different shapes, sizes, and orientations for a number of different clinical outcomes. Thus, the discussion of biomaterials or compositions may apply equally to the discussion on implants and vice versa.

According to one embodiment, the allograft compositions or implants prepared therefrom may be derived, for example, from intervertebral discs and/or umbilical cords. In an exemplary embodiment, the allograft includes viable cells. In other words, viable cells present in the allograft may be alive and capable of growth. The viable cells may be native to the intervertebral discs and/or umbilical cords that the allograft was derived from. In other words, native cells and/or other components of the allograft may include the original cells and tissues present in the intervertebral discs and/or umbilical cords when obtained from the donor. The native cells do not include exogenous, cultured, or expanded cells, although it is envisioned that such additional cells may be added to the allograft material, if desired. Similarly, the allograft may include only native tissues and components present in the intervertebral discs and/or umbilical cords when obtained from the donor or may be combined with other tissues, natural materials, synthetics, or other components, for example, suitable to promote tissue regeneration and improve the handling and delivery of the product to the target site.

When used for cartilage or disc repair, the allograft biomaterial compositions may be chondrogenic. Chondrification or chondrogenesis is the process in which cartilage is formed. The cartilage may be formed from condensed mesenchyme tissue, which differentiates into chondrocytes, and secretes the molecules that form extracellular matrix for cartilage repair. Once damaged, cartilage may have limited natural repair capabilities. Because chondrocytes are bound in lacunae, they may not be able to naturally migrate to damaged areas. Thus, the allograft biomaterial compositions may contain chondrocytes, chondrogenic precursors, or other properties suitable for promoting chondrogenesis, thereby ultimately promoting cartilage or disc repair.

When used for bone healing, the allograft biomaterial compositions may be osteogenic, osteoinductive, osteoconductive, and/or osteostimulative, which may be advantageous for tissue or bone healing and repair. The biomaterials may be osteoconductive when the material serves as a scaffold that provides surface area for new bone or tissue growth. The biomaterials may be osteoinductive if they stimulate osteoprogenitor cells or induce mesenchymal stem cells to differentiate into osteoblasts that then begin new bone or tissue formation. Biomaterials may be osteogenic if they contain cells (e.g., viable cells) that are capable of bone regeneration. The biomaterial may be osteostimulative if the material accelerates the bone or tissue formation process.

When used for other tissue healing or regeneration, the allograft biomaterial compositions may be configured to otherwise promote tissue healing. Tissue repair may be characterized by increased cell proliferation, capillary budding, and the synthesis of extracellular matrix (ECM) to fill in the damaged tissue. Thus, the allograft biomaterial compositions may contain cells, precursors, or other properties suitable for promoting tissue healing and repair. For example, other tissues may include epithelial tissue, connective tissue, muscle tissue, or nerve tissue.

The composition may also be "biocompatible" as that term refers to the ability (e.g., of a composition or material) to perform with an appropriate host response in a specific application, or at least to perform without having a toxic or otherwise deleterious effect on a biological system of the host, locally or systemically. The biomaterial and/or implant or a portion thereof may be "biologically degradable" in that the material may be degraded by cellular absorption and/or hydrolytic degradation in a patient's body.

According to one embodiment, the allograft biomaterial compositions may be configured to facilitate repair or regeneration of tissue, for example, bone, cartilage, or other tissue. In particular, the allograft biomaterial compositions may facilitate repair or regeneration of tissue at a target repair site. The target repair site can be, for example, a void, gap, or other defect, or a surgeon created opening in bone, cartilage, between bones, or other structure or tissue location in a body of a patient. The allograft biomaterial compositions may be configured to facilitate cartilage, bone, or other tissue growth at a target repair site. The allograft biomaterial compositions may be configured to be directly implanted or otherwise disposed at and in contact with the target repair site. The patient and target repair site may be in a human, mammal, or other organism.

Figure 2:
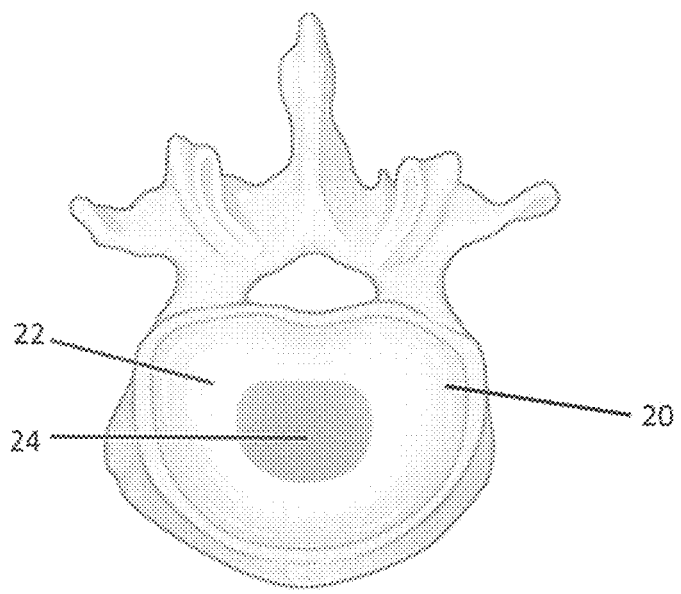
FIG. 2 depicts a superior view of the intervertebral disc shown in FIG. 1.

According to one embodiment, a composition for aiding tissue regeneration includes allograft derived from intervertebral disc. As best seen in FIGS. 1 and 2, an intervertebral disc 20 and intervertebral foramen 14 lie between adjacent vertebrae 10 in the vertebral column. Each disc 20 forms a fibrocartilaginous joint (a symphysis), to allow slight movement of the vertebrae 10, and acts as a ligament to hold the vertebrae 10 together. The intervertebral disc 20 contains two major components: the annulus fibrosus 22 and the nucleus pulposus 24. The nucleus pulposus 24 is the central region. The nucleus pulposus 24 is a hydrated gelatinous structure responsible for distributing loads. The nucleus pulposus 24 is an avascular, immune privileged tissue with high collagen II and proteoglycan content. The nucleus pulposus 24 contains various cell types including chondrocytic cells, notochordal cells and nucleus pulposus stem/progenitor cells. Encircling the nucleus pulposus 24, the annulus fibrosus 22 confers ligament-like restraint properties. The outer lamellae of the annulus fibrosus 22 contain small diameter sensory nerve fibers, which contribute to mechanotransduction. In addition to peripheral innervation, the annulus fibrosus 22 receives a small vascular supply from encircling veins and capillary networks. The annulus fibrosus 22 has a high collagen I content and contains fibrocytic cells.

In preparing the allograft, the intervertebral disc 20, with or without attached vertebrae 10, may be derived from healthy, cadaveric donor(s). The discs 20 may be derived from healthy human discs from the cervical, thoracic, and lumbar regions of the spine. The intervertebral disc 20 is preferably screened for various diseases, illicit drug use, and signs of degeneration. The intervertebral disc 20 is processed to obtain the resulting allograft. Preferably, the intervertebral disc 20 is derived from a human subject, although it is envisioned that the disc may be derived from other vertebrate animals.

The resulting allograft may comprise native collagen from the disc, native proteoglycan from the disc, and native viable cells from the disc. The native viable cells may include one or more of chondrocytic cells, notochordal cells, nucleus pulposus stem/progenitor cells, fibrocytic cells, and combinations thereof. The native collagen may include collagen I, collagen II, or both. The allograft may be derived from the nucleus pulposus, the annulus fibrosus, or both of the components of the intervertebral disc. When the nucleus pulposus is utilized, the allograft may contain collagen II, proteoglycan, chondrocytic cells, notochordal cells and nucleus pulposus stem/progenitor cells. When the annulus fibrosus is utilized, the allograft may contain collagen I and fibrocytic cells. Although specific tissues and cells are described here, it is understood that any of the other tissues and components known to be present in the native intervertebral disc may be present in the resulting allograft.

The intervertebral disc may be processed to obtain the allograft. For example, the discs may be processed to separate the disc from the vertebral bodies, and then rinsed, for example, in saline to remove any blood components. For example, the disc or allograft may be rinsed in a phosphate buffered saline multiple times. The phosphate buffered saline may contain one or more antibiotics, such as penicillin-streptomycin. The disc is preferably minimally manipulated to maintain all or most of the native disc cells.

The disc may be milled into particles, morselized, micronized, liquefied, or the native disc cells may be extracted therefrom. In an exemplary embodiment, the intervertebral disc is milled into particles. The particles may be uniform or non-uniform in shape and size. The particles may have a particle size, for example, ranging from about 100 microns to about 5 mm, about 150 microns to about 4 mm, about 250 microns to about 3 mm, about 250 microns to about 1 mm, or about 250 microns to about 750 microns. In some embodiments, it may be preferred that the particles are of a sufficiently small size that they are able to be injected, for example, through a syringe into a patient's disc space using a minimally invasive technique. After milling, the allograft particles may be further rinsed in saline, for example, phosphate buffered saline multiple times (e.g., 2 or 3 times) to remove any remaining blood components or contaminants.

Although it is envisioned that the disc-derived allograft may be used alone, it is also envisioned that the allograft may combined with other components. For example, one or more carriers, scaffold materials, or processing additives may be used with the allograft composition. Suitable carriers, scaffolds, or additives may include, but are not limited to, demineralized bone matrix (DBM) or other bone-derived components, ceramics including bioactive glasses or tricalcium phosphates, collagen including soluble and insoluble collagen, bone morphogenetic proteins (BMPs), phospholipids, carboxylmethylcellulose (CMC), glycerin, glycerol, polyethylene glycol (PEG), dextran, dextrose, hydrogels, poloxamers, polylactic acid (PLA), polylactic-co-glycolic acid (PLGA), other copolymers of the same family, and combinations thereof.

Additionally, biological agents may be added to the biomaterial or implant, such as bone growth factors such as platelet derived growth factor (PDGF), vascular endothelial growth factor (VEGF), insulin derived growth factor (IDGF), a keratinocyte derived growth factor (KDGF), or a fibroblast derived growth factor (FDGF), stem cells, and platelet rich plasma (PRP), to name a few. If desired, one or more active pharmaceutical ingredients or medicaments may be incorporated into the biomaterial or implant as well.

Biological agents may be added in any suitable pharmaceutically acceptable and effective amounts known in the art.

After processing, the allograft may be preserved. For example, the allograft may be preserved with a cryoprotectant and frozen for later use. The cryoprotectant may include minimum essential medium, dimethyl sulfoxide (e.g., 10% DMSO), glycerol, polyethylene glycol (PEG), dextran, dextrose, or a combination thereof. The allograft may be mixed with the cryoprotectant and frozen at a temperature between −80° C. and −180° C., preferably at either −80° C. or −180° C. When ready to be implanted in a patient, the frozen mixture may be thawed and the cryoprotectant may be decanted prior to use.

In another exemplary embodiment, the allograft particles may be combined with a carrier solution. If present, the carrier solution may include one or more of hyaluronic acid (HA), collagen, aggrecan, chondroitin sulfate, polyethylene glycol (PEG), dextran, dextrose, or other suitable carriers. The carrier solution may also contain growth factors, such as transforming growth factor (TGF-B) and/or growth differentiation factor (GDF). The final particle and carrier solution may be implanted in the patient. The allograft particles may be combined with the carrier solution before freezing or after decanting the cryoprotectant. For example, at the time of the surgical procedure, the particles may be thawed, the cryoprotectant decanted, and the allograft particles combined with the carrier solution.

In another embodiment, the native cells may be cultured. The particles may be rinsed in saline, for example, phosphate buffered saline multiple times (e.g., 2 or 3 times). After the rinse, the particles may be cultured in medium, for example, for up to 10 days. The medium may contain minimum essential medium or Dulbecco's Modified Eagle's Medium with or without the following supplements: dexamethasone, Penicillin-Streptomycin, ascorbic acid, bovine serum albumin (BSA), linoleic acid (LA), insulin, transferrin, selenous acid, proline, and growth factors (TGF-B and/or GDF). Supplements may increase cell count and maintain a nucleus pulposus-like phenotype. At the end of the culture period, the particles with proliferated cells may be placed in cryoprotectant and frozen, for example, at −80° C. or −180° C.

According to another embodiment, the allograft particles may be treated with an enzyme and/or cultured. For example, the allograft particles may be treated with one or more enzymes, including protease and/or collagenase, for a suitable duration with periodic agitation. The supernatant may be filtered through a cell strainer, and the resulting cell suspension may be centrifuged. The enzyme solution may be aspirated, and the cell pellet may be resuspended in cell culture media. The cell solution may be plated in a tissue culture flask and cultured, for example, for up to 10 days. At the end of the culture period, the cells are detached using a dissociation agent and seeded with original extracellular matrix particles. The cells and extracellular matrix particles are placed in cryoprotectant, as described herein, and frozen. At the time of the surgical procedure, the cells and extracellular matrix particles may be thawed and implanted in the patient. Alternatively, the cells and extracellular matrix particles may be combined with a carrier solution as described herein. The resulting solution may be implanted in the patient.

The resulting allografts may be particularly suitable for intervertebral disc repair. Due to minimal processing, the living cells remain viable in or on the allograft. The human allograft, derived from intervertebral disc, may be used, for example, to treat degenerative disc disease (DDD) and may be a suitable replacement for spinal fusion surgery.

Figure 3:
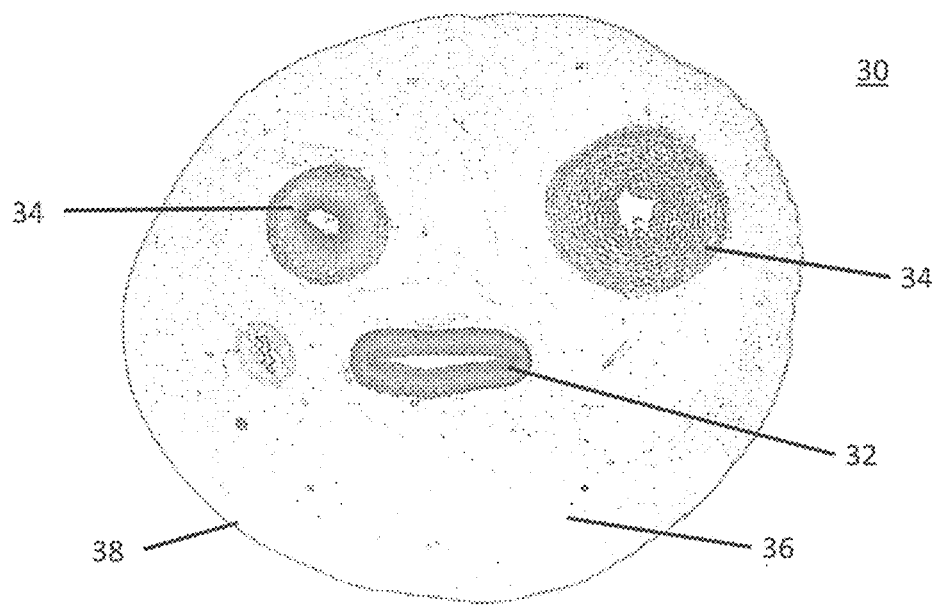
FIG. 3 is a cross-sectional view of an umbilical cord.
Figure 4:
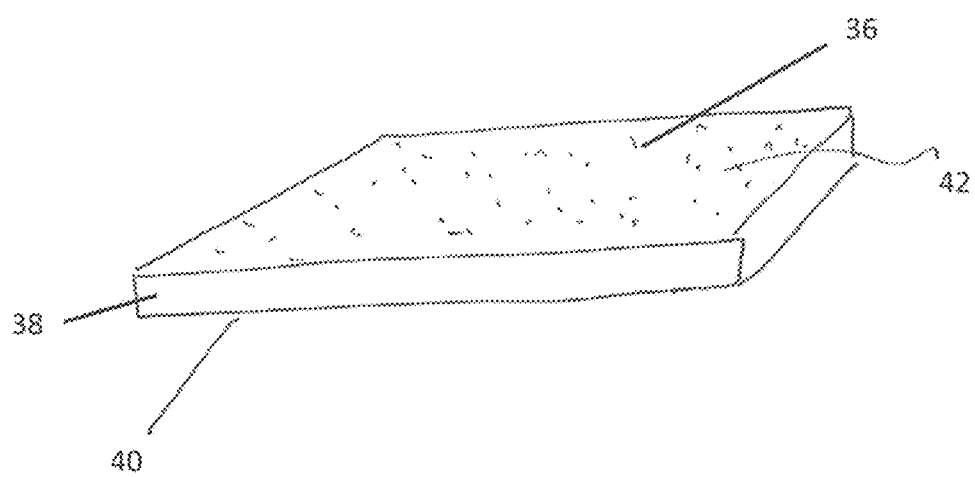
FIG. 4 depicts a patch derived from umbilical cord according to one embodiment.

According to another embodiment, a composition for aiding tissue regeneration may include an allograft derived from umbilical cord. The umbilical cord is a conduit between the developing embryo or fetus and the placenta. As best seen in FIGS. 3 and 4, the umbilical cord 30 contains one vein 32, which carries oxygenated, nutrient-rich blood to the fetus, and two arteries 34 that carry deoxygenated, nutrient-depleted blood away. The umbilical cord 30 contains Wharton's jelly 36, a gelatinous substance made largely from mucopolysaccharides which protects the blood vessels inside. The umbilical cord 30 is surrounded by cord lining or umbilical cord lining membrane 38, which is the outermost layer of the umbilical cord 30. The umbilical cord lining membrane 38 comprises two layers: the amniotic or epithelial layer 40 and the sub-amniotic or mesenchymal layer 42. The umbilical cord lining membrane 38 is a rich source of two strains of stem cells: epithelial stem cells (from the epithelial layer 40) and mesenchymal stem cells (from the mesenchymal layer 42).

In preparing the allograft, the umbilical cord 30, with or without attached placentas, may be obtained from volunteer donors. In particular, donors may include mothers who have undergone an elective Caesarian procedure for childbirth. The umbilical cord 30 is preferably screened for various diseases, illicit drug use, and signs of degeneration. The umbilical cord 30 is processed to obtain the resulting allograft. Preferably, the umbilical cord 30 is derived from a human subject, although it is envisioned that the cord may be derived from other mammals.

The resulting allograft may comprise the native umbilical cord lining membrane, native viable cells including native epithelial stem cells and native mesenchymal stem cells, and/or native Wharton's jelly. Although specific tissues and cells are described here, it is understood that any of the other tissues and components known to be present in the native cord may be present in the resulting allograft.

The umbilical cord may be processed to obtain the allograft. The veins and arteries may be removed and separated from the remainder of the umbilical cord. The remaining umbilical cord may comprise Wharton's jelly and amniotic epithelium. The umbilical cord product is preferably minimally manipulated such that any native viable cells, such as the native mesenchymal stem cells and native epithelial stem cells, remain in the final product. The layer may be processed into a patch or sheet suitable for use in bone, cartilage, and/or tissue healing or other medical applications. For example, the patch may have a given length, width, and thickness. The patch may be square, rectangular, round, or of other suitable shape. The length may range from about 1 cm to about 8 cm. The width may range from about 1 cm to about 4 cm. When round, the diameter may range from about 10 mm-16 mm. The thickness would be determined by the natural umbilical cord as obtained from the mother. The resulting patch may include an upper layer of native Wharton's jelly and mesenchymal stem cells and a lower layer of native amniotic epithelium and epithelial stem cells. The patch may be preserved, dried, rehydrated, or otherwise stored prior to use.

The patch may be applied to or otherwise integrated with another framework, structures, scaffold, or cage. For example, the umbilical-derived patch or a portion thereof may be applied to the upper and lower contact surfaces of an intervertebral spacer or implant. Examples of such implants are disclosed in U.S. Publication No. 2017/0202678, which is incorporated by reference herein in its entirety for all purposes.

In the alternative, if a patch or sheet is not desired, the umbilical cord allograft may be further processed, for example, milled, morselized, liquefied, or combined with other ingredients (e.g., living cells, bone-based products, etc.) to obtain the resultant product.

Although it is envisioned that the umbilical cord-derived allograft may be used alone, it is also envisioned that the allograft may combined with other components. For example, one or more carriers, scaffold materials, or processing additives may be used with the allograft composition. Suitable carriers, scaffolds, or additives may include, but are not limited to, demineralized bone matrix (DBM) or other bone-derived components, ceramics including bioactive glasses or tricalcium phosphates, collagen including soluble and insoluble collagen, bone morphogenetic proteins (BMPs), phospholipids, carboxylmethylcellulose (CMC), glycerin, glycerol, polyethylene glycol (PEG), hydrogels, poloxamers, polylactic acid (PLA), polylactic-co-glycolic acid (PLGA), other copolymers of the same family, and combinations thereof.

Additionally, biological agents may be added to the biomaterial or implant, such as bone growth factors such as platelet derived growth factor (PDGF), vascular endothelial growth factor (VEGF), insulin derived growth factor (IDGF), a keratinocyte derived growth factor (KDGF), or a fibroblast derived growth factor (FDGF), stem cells, and platelet rich plasma (PRP), to name a few. If desired, one or more active pharmaceutical ingredients or medicaments may be incorporated into the biomaterial or implant as well. Biological agents may be added in any suitable pharmaceutically acceptable and effective amounts known in the art.

The human allograft, derived from umbilical cord, may be used in a variety of surgical procedures. Due to minimal processing, living cells may remain viable in or on the allograft. The allograft may be suitable for use in bone, cartilage, and/or tissue healing or other medical applications where living cells are needed.

In yet another embodiment, the umbilical cord may be decellularized using enzyme digestion and used as a scaffold or membrane as is, or may be seeded with exogenous mesenchymal stem cells, for example, isolated from bone or bone marrow aspirate to promote bone regeneration.

The allograft biomaterials described herein and/or implants formed therefrom are intended to be applied at a tissue, bone or cartilage repair site, e.g., one resulting from injury or defect. The implant can be utilized in a wide variety of orthopedic, periodontal, neurosurgical, oral and maxillofacial surgical procedures. In particular, the biomaterials may be suitable for repairs of the vertebral column including spinal fusion and internal fixation; tumor surgery, e.g., deficit filling; discectomy; laminectomy; scoliosis, lordosis and kyphosis treatments. Possible clinical applications may include e.g., the treatment of spinal disc degeneration or disease, traumatic, pathologic, or stress fractures, congenital defects or fractures, or operative defects in any bone or between bones of the body.

The compositions and implants may be configured for use at various target repair sites within a body of a patient to facilitate bone, cartilage, and/or tissue growth therein. In some embodiments, the composition is configured for use at a target repair site in the patient's spine. For example, the composition can facilitate chondrogenic repair of the intervertebral disc between adjacent vertebrae. In another example, the composition can facilitate growth of bone between the body of a first vertebra and the body of a second vertebra to achieve interbody fusion of the two vertebrae. In a spinal fusion procedure, the composition may be used in conjunction with one or more mechanical supports (e.g., a cage or frame, spacer, plate, a plurality of screws and/or rods, or the like). Although the spine is described, the composition can be configured to be implanted into or at a target repair site in or at a different cartilage, bone, tissue or other structures of the patient's body.

The term "treating" and the phrases "treatment of a disease" and "treatment of a condition" refer to executing a protocol that may include the use of the compositions, devices and methods herein and/or administering one or more biomaterials to a patient (human, normal or otherwise, or other mammal), in an effort to alleviate signs or symptoms of the disease or condition. Alleviation can occur prior to signs or symptoms of the disease or condition appearing, as well as after their appearance. Thus, "treating" or "treatment" includes "preventing" or "prevention" of disease or undesirable condition. In addition, "treating" or "treatment" does not require complete alleviation of signs or symptoms and does not require a cure to the ailment.

Further example embodiments are directed to kits that include components for making the present biomaterials and implants, including for example, carriers or scaffolds, cages (e.g., titanium and/or polyether ether ketone (PEEK) spacers), allograft spacers, demineralized bone materials, cell culture media, phosphate buffered saline (PBS), a tissue culture substrate such as a flask, trypsin, or mixtures, bone graft harvesting tools, bone marrow aspirate retrieval tools, or the like. Additional components, instructions and/or other apparatus may also be included.

The following examples are provided to further illustrate various non-limiting embodiments and techniques. It should be understood, however, that these examples are meant to be illustrative and do not limit the scope of the claims. As would be apparent to skilled artisans, many variations and modifications are intended to be encompassed within the spirit and scope of the invention.

EXPERIMENTAL EXAMPLES

In each of the examples described below intervertebral disc is screened for various diseases, illicit drug use, and signs of degeneration. Surrounding soft tissues, such as tendon, muscle, and fat, are removed from the spine, and the intervertebral disc (without endplates) is dissected from the vertebrae. The intervertebral disc is washed in a phosphate buffered saline solution containing antibiotics (1-2% Penicillin-Streptomycin) 2-3 times. The intervertebral disc is minimally manipulated such that any native viable cells remain in the final product. The allograft includes nucleus pulposus, annulus fibrosus, or a combination of both tissues. The tissue is milled to particles (250 micron-3 mm size). The disc particles are rinsed with 0.9% saline 2-3 times. After the rinse, the particles are treated in one of the following ways:

Example 1: Disc Derived Allograft Particles

The particles are rinsed in phosphate buffered saline 2-3 times. The particles are mixed with a cryoprotectant (minimum essential medium and 10% Dimethyl Sulfoxide) and frozen at either −80° C. or −180° C. Immediately prior to use, the mixture is thawed and the cryoprotectant decanted.

Example 2: Disc Derived Allograft Particles and Carrier Solution

The particles are rinsed in phosphate buffered saline 2-3 times. After the rinse, the particles are placed in cryoprotectant and frozen at either −80° C. or −180° C. At the time of the surgical procedure, the particles are thawed and combined with a carrier solution containing one or more of the following: hyaluronic acid (HA), collagen, aggrecan, chondroitin sulfate, and/or polyethylene glycol (PEG). The carrier solution may also contain growth factors, such as transforming growth factor (TGF-B) and/or growth differentiation factor (GDF). The final particle and carrier solution are then implanted in the patient.

Example 3: Disc Derived Allograft Particles with Cultured Cells

The particles are rinsed in phosphate buffered saline 2-3 times. After the rinse, the particles are cultured in medium for up to 10 days. The medium may contain minimum essential medium or Dulbecco's Modified Eagle's Medium with or without the following supplements: dexamethasone, Penicillin-Streptomycin, ascorbic acid, bovine serum albumin (BSA), linoleic acid (LA), insulin, transferrin, selenous acid, proline, and growth factors (TGF-B and/or GDF). Supplements may increase cell count and maintain an NP-like phenotype. At the end of the culture period, the particles with proliferated cells may be placed in a cryoprotectant and frozen at either −80° C. or −180° C.

Example 4: Disc Derived Allograft Particles with Cultured Cells and Carrier Solution The particles are rinsed in phosphate buffered saline 2-3 times. After the rinse, the particles are cultured in medium for up to 10 days. The medium may contain minimum essential medium or Dulbecco's Modified Eagle's Medium with or without the following supplements: dexamethasone, Penicillin-Streptomycin, ascorbic acid, bovine serum albumin (BSA), linoleic acid (LA), insulin, transferrin, selenous acid, proline, and growth factors (TGF-B and/or GDF). Supplements may increase cell count and maintain an NP-like phenotype. At the end of the culture period, the particles with proliferated cells may be placed in a cryoprotectant and frozen at either −80° C. or −180° C. At the time of the surgical procedure, the particles are thawed and may be optionally combined with a carrier solution containing one or more of the following: hyaluronic acid (HA), collagen, aggrecan, chondroitin sulfate, and/or polyethylene glycol (PEG). The carrier solution may also contain growth factors, such as transforming growth factor (TGF-B) and/or growth differentiation factor (GDF). The final particle and carrier solution are then implanted in the patient.

Example 4: Disc Derived Allograft Particles Treated with Enzymes

The particles may be treated with protease (e.g., Pronase® 1 mg/ml-10 mg/ml) and/or collagenase (1 mg/ml-10 mg/ml) for a total of 1-4 hours at 37° C., with periodic agitation. The supernatant is filtered through a 40 μm-100 μm cell strainer, and the resulting cell suspension is centrifuged at 300 rcf for 5-15 minutes. The protease solution is aspirated, and the cell pellet is resuspended in cell culture media. The cell solution is plated in a tissue culture flask and cultured for up to 10 days. At the end of the culture period, the cells are detached using a dissociation agent and seeded with original extracellular matrix particles. The cells and extracellular matrix particles are placed in cryoprotectant and frozen at either −80° C. or −180° C. At the time of the surgical procedure, the cells and extracellular matrix particles are thawed and optionally combined with a carrier solution. The carrier solution may contain one or more of the following: hyaluronic acid (HA), collagen, aggrecan, chondroitin sulfate, and/or polyethylene glycol (PEG). The carrier solution may also contain growth factors, such as transforming growth factor (TGF-B) and/or growth differentiation factor (GDF). The resulting solution is implanted in the patient.

Although the invention has been described in example embodiments, those skilled in the art will appreciate that various modifications may be made without departing from the spirit and scope of the invention. It is therefore to be understood that the inventions herein may be practiced other than as specifically described. Thus, the present embodiments should be considered in all respects as illustrative and not restrictive. Accordingly, it is intended that such changes and modifications fall within the scope of the present invention as defined by the claims appended hereto.

What is claimed is:

1. A method for manufacturing an allograft composition for aiding tissue regeneration, the method comprising:
    milling a mammalian intervertebral disc to obtain allograft particles, wherein the intervertebral disc comprises native collagen, native proteoglycan, and native viable cells; and
    mixing a cryoprotectant with the allograft particles to preserve the composition,
    wherein the allograft particles are milled from the human intervertebral disc after the intervertebral disc has been treated with a phosphate buffered saline solution containing an antibiotic;
    providing a carrier solution, wherein the carrier solution includes one or more of hyaluronic acid (HA), collagen, aggrecan, chondroitin sulfate, and polyethylene glycol (PEG);
    culturing the particles in a medium to obtain particles with proliferated cells; and
    treating the particles with enzymes, including protease, for one to four hours at 37° C. with periodic agitation, wherein the particles with the enzymes are aspirated and a corresponding cell pellet is resuspended in a cell culture media and cultured for up to 10 days, and at the end of a culture period the cell culture is detached using a dissociation agent and seeded with original extracellular matrix particles.

2. The method of claim 1, wherein the native viable cells comprise chondrocytic cells, notochordal cells, nucleus pulposus stem/progenitor cells, fibrocytic cells, or a combination thereof.

3. The method of claim 1, wherein the native collagen includes collagen I, collagen II, or both.

4. The method of claim 1, wherein the intervertebral disc includes nucleus pulposus, annulus fibrosus, or both.

5. The method of claim 1, wherein the particles have a particle size ranging from about 250 microns to about 3 mm.

6. The method of claim 1, wherein the particles have a particle size ranging from over 400 microns to about 3 mm.

7. The method of claim 1, further comprising providing a carrier including demineralized bone matrix (DBM).

8. The method of claim 1, further comprising providing a carrier including bioactive glass.

9. The method of claim 1, further comprising providing a carrier including tricalcium phosphates.

10. The method of claim 1, further comprising providing a carrier including one or more of the following: bone morphogenetic proteins (BMPs), phospholipids, carboxylmethylcellulose (CMC), glycerin, glycerol, dextran, dextrose, hydrogels, poloxamers, polylactic acid (PLA), and polylactic-co-glycolic acid (PLGA).

11. The method of claim 1, further comprising providing a biological agent including one or more of the following: a platelet derived growth factor (PDGF), a vascular endothelial growth factor (VEGF), a insulin derived growth factor (IDGF), a keratinocyte derived growth factor (KDGF), a fibroblast derived growth factor (FDGF), stem cells, and platelet rich plasma (PRP).

12. The method of claim 1, further comprising freezing the cells at either −80° C. or −180° C. and thawing the cells prior to implantation.

* * * * *